United States Patent
Yokogawa

(10) Patent No.: US 9,664,559 B2
(45) Date of Patent: May 30, 2017

(54) IMAGE CAPTURE DEVICE AND ELECTRONIC APPARATUS

(71) Applicant: Sony Semiconductor Solutions Corporation, Kanagawa (JP)

(72) Inventor: Sozo Yokogawa, Kanagawa (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 0 days.

(21) Appl. No.: 14/311,958

(22) Filed: Jun. 23, 2014

(65) Prior Publication Data

US 2015/0002843 A1  Jan. 1, 2015

(30) Foreign Application Priority Data

Jun. 28, 2013 (JP) ................................ 2013-136220

(51) Int. Cl.
*G01J 3/02* (2006.01)
*G01N 21/552* (2014.01)
*G02B 5/00* (2006.01)
*G01N 21/41* (2006.01)

(52) U.S. Cl.
CPC .......... *G01J 3/0205* (2013.01); *G01N 21/554* (2013.01); *G02B 5/008* (2013.01); *G01N 21/4133* (2013.01)

(58) Field of Classification Search
CPC .................................................. G01J 3/0229
See application file for complete search history.

(56) References Cited

U.S. PATENT DOCUMENTS

| | | | |
|---|---|---|---|
| 2006/0279737 A1* | 12/2006 | Chinowsky | G01N 21/553 356/445 |
| 2008/0079938 A1* | 4/2008 | Choi | G01J 3/02 356/318 |
| 2012/0293854 A1* | 11/2012 | Zheludev et al. | 359/244 |
| 2013/0065777 A1* | 3/2013 | Altug et al. | 506/9 |
| 2014/0151733 A1* | 6/2014 | Koike et al. | 257/98 |

OTHER PUBLICATIONS

Chang, Tsung-Yao, et al. "Large-scale plasmonic microarrays for label-free high-throughput screening." Lab on a Chip 11.21 (2011): 3596-3602.*

Yanik et al., "An Optofluidic Nanoplasmonic Biosensor for Direct Detection of Live Viruses from Biological Media", Nano Letters, American Chemical Society, 2010, 8 pages.

* cited by examiner

*Primary Examiner* — Kara E Geisel
*Assistant Examiner* — Shawn Decenzo
(74) *Attorney, Agent, or Firm* — Sheridan Ross P.C.

(57) ABSTRACT

There is provided an image capture device including a narrow-band optical irradiation system including a light source, a solid-state imaging element including an array of pixels and sensitive to a predetermined range of wavelengths, and a metal thin-film filter provided in an optical path between the optical irradiation system and the solid-state imaging element, and having a periodic microstructural pattern having a period shorter than a wavelength detected by the solid-state imaging element.

16 Claims, 20 Drawing Sheets

PRIOR ART

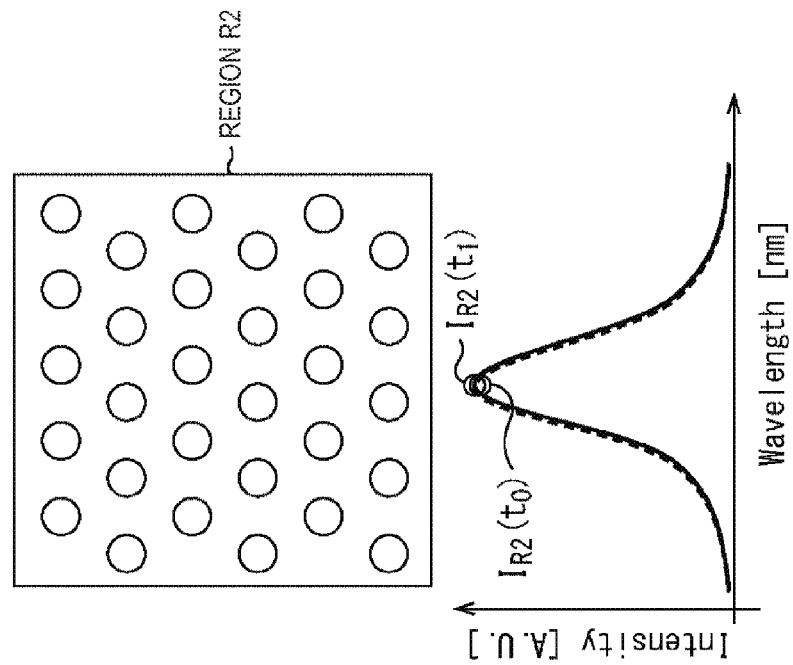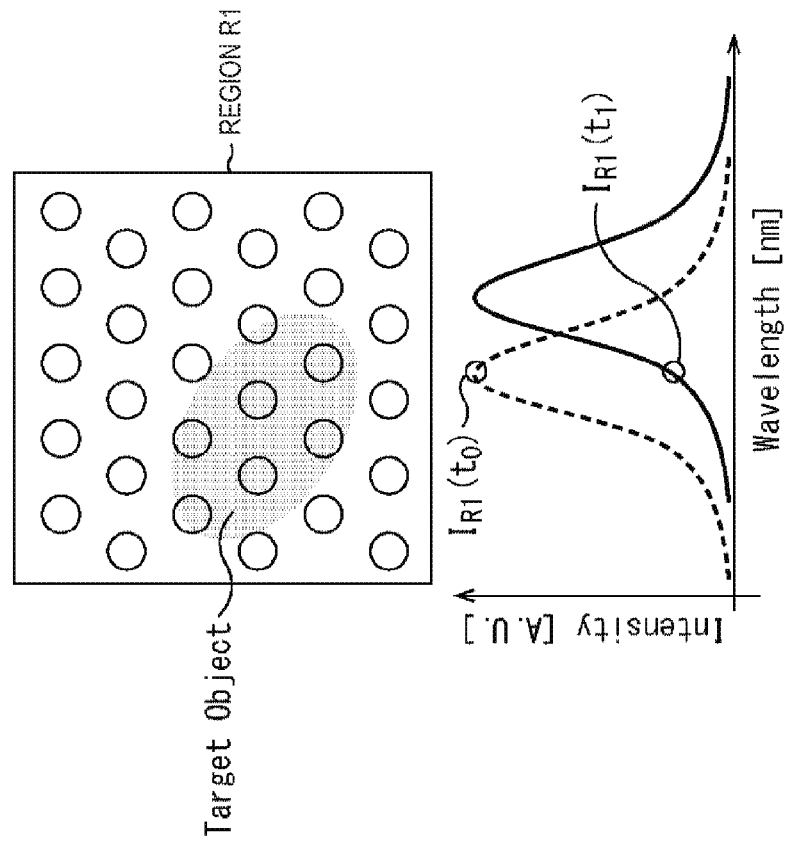
FIG. 15

Hole Array

112 METAL THIN-FILM FILTER

Dot Array

112 METAL THIN-FILM FILTER

Coaxial Hole Array

112 METAL THIN-FILM FILTER

Ring Array

112 METAL THIN-FILM FILTER

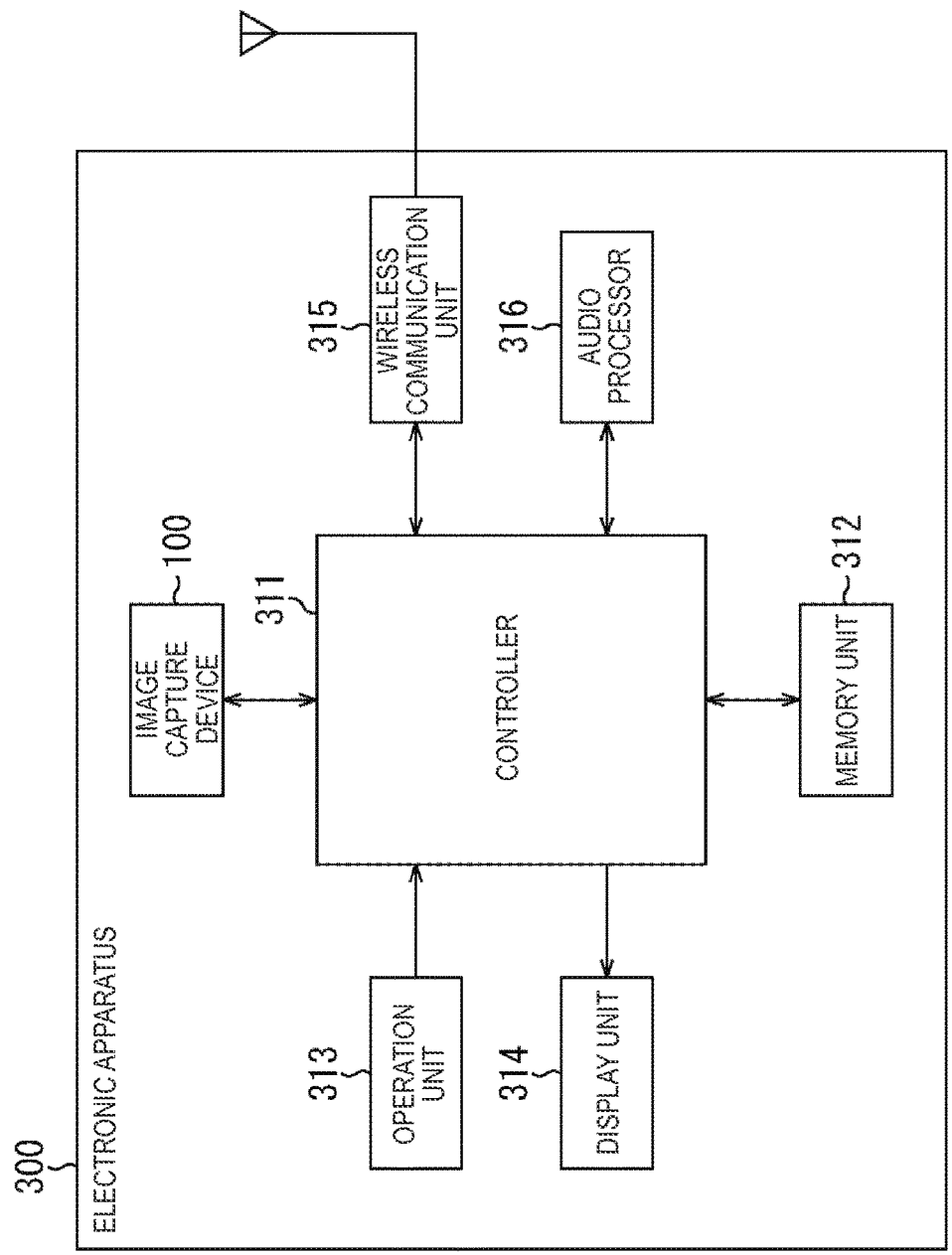

IMAGE CAPTURE DEVICE AND ELECTRONIC APPARATUS

CROSS-REFERENCE TO RELATED APPLICATIONS

This application claims the benefit of Japanese Priority Patent Application JP 2013-136220 filed Jun. 28, 2013, the entire contents of which are incorporated herein by reference.

BACKGROUND

The present technology relates to image capture devices and electronic apparatuses, and more particularly, to an image capture device and an electronic apparatus which are low in cost and simple in configuration and can measure a target object.

As examples of practical use of a filter using surface plasmon polaritons (SPPs) (hereinafter referred to as a "metal thin-film filter"), there have been reports that the filter is used to monitor the growth of viruses or bacteria or test the sensitivity of antibodies (see, for example, Yanik, A. A. et al., Nano Letters 10 (12), 4962-4969 (2010)).

As schematically shown in FIG. 1, in order to perform such measurement, a configuration is employed in which the metal thin-film filter is provided in an optical path between a light source and a spectrometer. In the configuration, the metal thin-film filter is irradiated with light from the light source, and the spectrum of light transmitted therethrough is measured using the spectrometer, whereby a target object which is attached to the metal thin-film filter is measured.

Specifically, if, for example, viruses or bacteria are attached to antigens or antibodies immobilized on a surface of the metal thin-film filter to change the refractive index of surroundings of the metal thin-film filter, the spectral distribution of the transmitted light is shifted.

FIG. 2 shows a transmission wavelength profile of the metal thin-film filter, where the horizontal axis represents wavelengths and the vertical axis represents transmission efficiencies. A waveform A indicates a transmission spectrum in an initial state in which viruses etc. have not been attached, and waveforms B and C indicate transmitted light spectra which are obtained after a predetermined time has passed since the initial state, i.e., after viruses etc. have been attached. As can be seen from these waveforms, the peak wavelength of the transmission spectrum is shifted to longer wavelengths as time passes.

In measurement techniques in the related art, the change amount of the refractive index of surroundings of the metal thin-film filter is obtained by measuring the amount of such a shift of the peak wavelength of the transmission spectrum using a spectrometer, and based on the change amount, the amount of viruses or bacteria present on the metal thin-film filter is determined.

SUMMARY

However, in the above measurement technique in the related art, it is necessary to employ a spectrometer for measuring the shift amount of the peak wavelength of the transmission spectrum. In general, devices equipped with a spectrometer are high in cost and complex in configuration. Therefore, there has been a demand for a device which is low in cost and simple in configuration and can measure a target object.

With these circumstances in mind, the present technology has been made to measure a target object using, at low cost and with a simple configuration.

According to a first embodiment of the present disclosure, there is provided an image capture device including a narrow-band optical irradiation system including a light source, a solid-state imaging element including an array of pixels and sensitive to a predetermined range of wavelengths, and a metal thin-film filter provided in an optical path between the optical irradiation system and the solid-state imaging element, and having a periodic microstructural pattern having a period shorter than a wavelength detected by the solid-state imaging element.

The metal thin-film filter may have a property that a spectral distribution of transmitted light is shifted in a wavelength direction due to a difference between the refractive index of a target object tightly attached or located close to the metal thin-film filter and a refractive index of a medium with which a space around the metal thin-film filter is filled. The image capture device may further include a signal processor configured to detect a change in signal intensity of the solid-state imaging element, the change in signal intensity corresponding to a change in transmission efficiency corresponding to the shift of the spectral distribution of transmitted light in the wavelength direction.

The metal thin-film filter may be a thin film of an elemental metal or an alloy and having a thickness of 500 nm or less.

The metal thin-film filter may have at least one periodic microstructural pattern in a surface of the metal thin-film filter, and a fundamental period of the microstructural pattern is not longer than approximately a wavelength of visible light.

The metal thin-film filter may have, as the microstructural pattern, a hole array structure including openings having a diameter of 500 nm or less arranged in a honeycomb array or an orthogonal matrix array.

The metal thin-film filter may have, as the microstructural pattern, a dot array structure including dot-like structures having a diameter of 500 nm or less arranged in a honeycomb array or an orthogonal matrix array.

The metal thin-film filter may have, as the microstructural pattern, a coaxial hole array structure including openings having a diameter of 500 nm or less arranged in a honeycomb array or an orthogonal matrix array, each opening having a coaxial structure in which a dot-like structure is provided at a center of the opening.

The metal thin-film filter may have, as the microstructural pattern, a ring array structure including dot-like structures having a diameter of 500 nm or less arranged in a honeycomb array or an orthogonal matrix array, each dot-like structure having a ring-like structure in which an opening having a diameter smaller than a diameter of the dot-like structure is provided at a center of the dot-like structure.

In the solid-state imaging element, the array of pixels may be divided into a plurality of blocks. In the metal thin-film filter, regions corresponding to adjacent blocks may have the same microstructural pattern. The signal processor may obtain a difference between signals detected by pixels in adjacent blocks to correct an offset between the pixels in the adjacent blocks.

The light source may emit light having a narrow band of wavelengths.

The light source may be a light emitting diode (LED) light source or a laser light source configured to selectively emit electromagnetic waves having a narrow band of wavelengths of a wavelength band to which the solid-state imaging element is sensitive.

The solid-state imaging element may be sensitive to a wavelength range of visible light or near-infrared light.

The metal thin-film filter may be removably attached in the optical path.

The image capture device according to the first embodiment of the present disclosure may include a narrow-band optical irradiation system including a light source, a solid-state imaging element including an array of pixels and sensitive to a predetermined range of wavelengths, and a metal thin-film filter provided in an optical path between the optical irradiation system and the solid-state imaging element, and having a periodic microstructural pattern having a period shorter than a wavelength detected by the solid-state imaging element.

According to a second embodiment of the present disclosure, there is provided an electronic apparatus including an image capture device including a narrow-band optical irradiation system including a light source, a solid-state imaging element including an array of pixels and sensitive to a predetermined range of wavelengths, and a metal thin-film filter provided in an optical path between the optical irradiation system and the solid-state imaging element, and having a periodic microstructural pattern having a period shorter than a wavelength detected by the solid-state imaging element.

The electronic apparatus according to the second embodiment of the present disclosure may include an image capture device including a narrow-band optical irradiation system including a light source, a solid-state imaging element including an array of pixels and sensitive to a predetermined range of wavelengths, and a metal thin-film filter provided in an optical path between the optical irradiation system and the solid-state imaging element, and having a periodic microstructural pattern having a period shorter than a wavelength detected by the solid-state imaging element.

According to the first and second aspects of the present technology, a target object can be measured at low cost and with a simple configuration.

BRIEF DESCRIPTION OF THE DRAWINGS

FIG. 15 is a diagram showing the intensity of light detected at pixels of each of adjacent blocks;

FIG. 20 is a diagram showing a configuration of an embodiment of an electronic apparatus to which the present technology is applied.

DETAILED DESCRIPTION OF THE EMBODIMENT(S)

Figure 1:
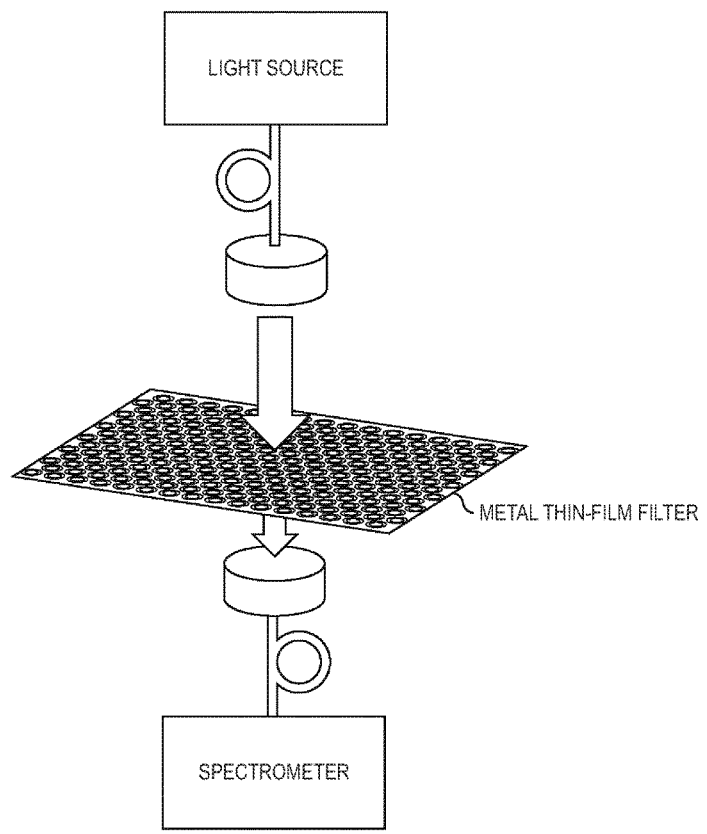
FIG. 1 is a diagram for describing a configuration in the related art.
Figure 2:
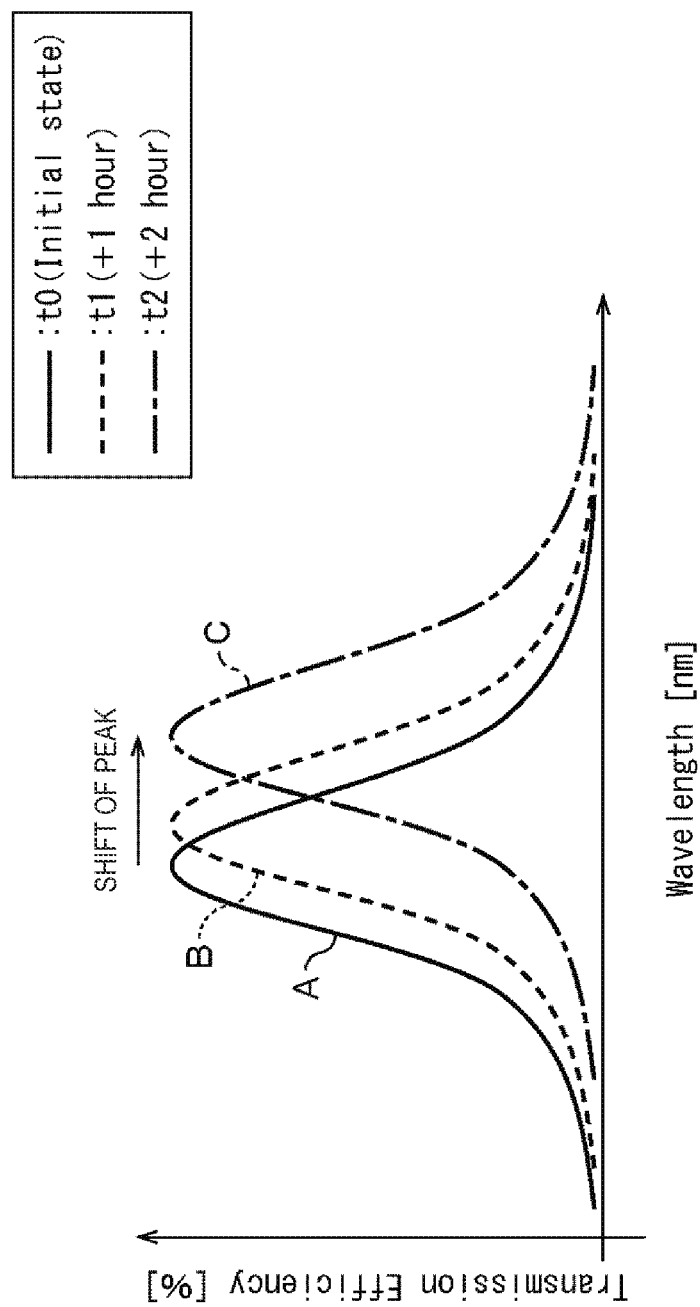
FIG. 2 is a diagram for describing a measurement technique in the related art.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

<Configuration of Image Capture Device>

Figure 3:
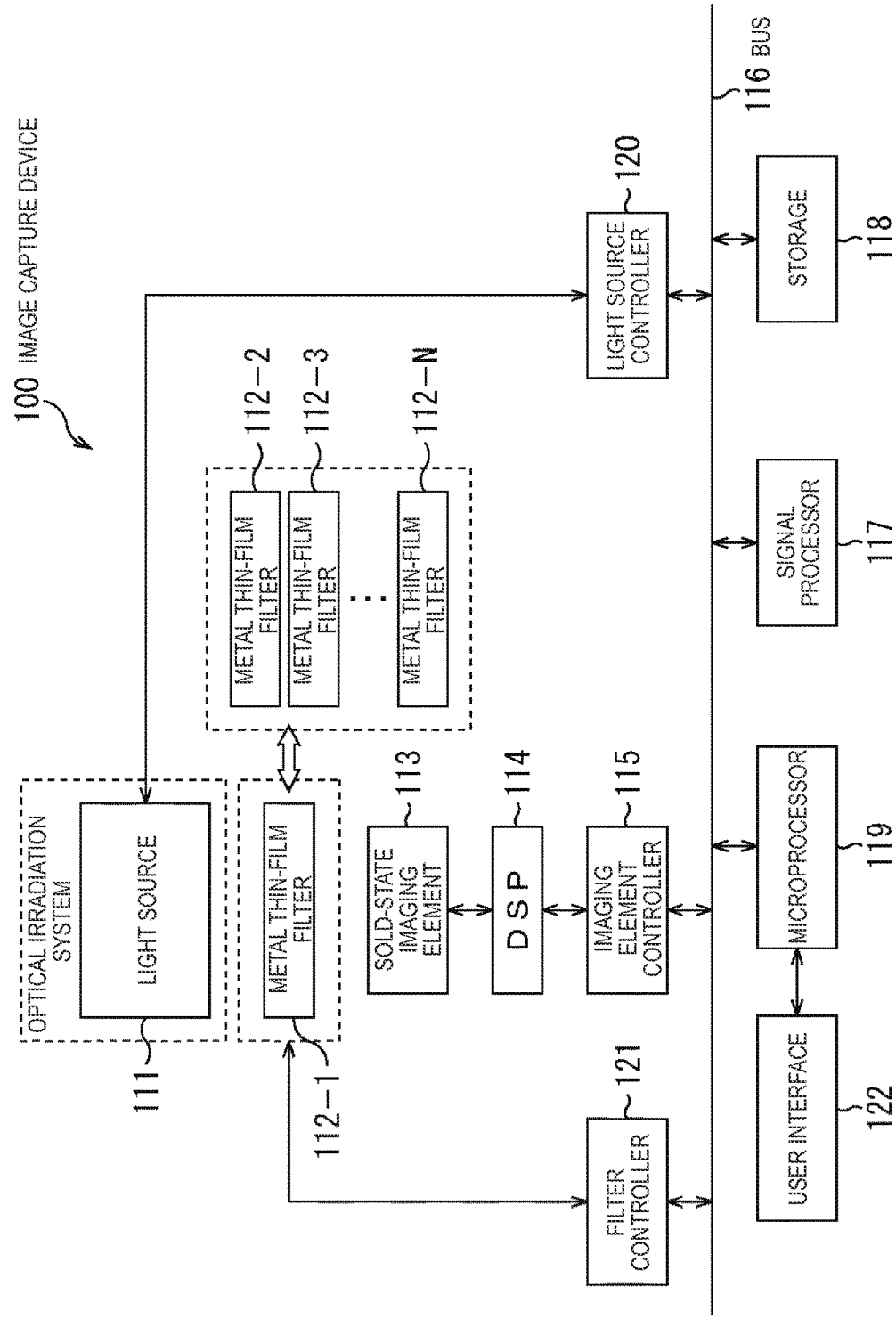
FIG. 3 is a diagram showing a configuration of an embodiment of an image capture device to which the present technology is applied.

FIG. 3 is a diagram showing a configuration of an embodiment of an image capture device to which the present technology is applied.

The image capture device 100 of FIG. 3 has a function of measuring a target object. As shown in FIG. 3, the image capture device 100 includes a light source 111, a metal thin-film filter 112-1, a solid-state imaging element 113, a DSP 114, an imaging element controller 115, a bus 116, a signal processor 117, a storage 118, a microprocessor 119, a light source controller 120, a filter controller 121, and a user interface 122.

The light source 111 is included in an optical irradiation system including a lens, a filter, etc. The light source 111 is a monochromatic surface light source which can selectively emit electromagnetic waves having a narrow band of wavelengths, such as a light emitting diode (LED) light source, a laser light source, etc. Light emitted from the light source 111 is transmitted through the metal thin-film filter 112-1, and then received by a light receiving surface of the solid-state imaging element 113.

The metal thin-film filter 112-1 is a thin film of an elemental metal, such as gold (Au), silver (Ag), aluminum (Al), etc., or an alloy thereof, and has a thickness of 500 nm or less. The metal thin-film filter 112-1 has, on a surface thereof, a periodic microstructural pattern on a sub-wavelength scale with respect to a wavelength detected by the solid-state imaging element 113.

Note that, as shown in FIG. 3, the metal thin-film filter 112-1 may be removably attached by a predetermined mechanism, and instead of the metal thin-film filter 112-1, any of metal thin-film filters 112-2 to 112-N (where N is an integer of one or more) having different microstructural patterns on a surface thereof may be attached and provided in the optical path between the light source 111 and the solid-state imaging element 113. In the description that follows, the metal thin-film filters 112-1 to 112-N are simply referred to as metal thin-film filters 112 when no distinction is necessary.

The solid-state imaging element 113 is, for example, a two-dimensional solid-state imaging element which includes an array of pixels and is sensitive to a wavelength range of visible or near-infrared light, such as a complementary metal-oxide semiconductor (CMOS) image sensor, a charge coupled device (CDD) image sensor, etc.

The solid-state imaging element 113 receives light which has been emitted from the light source 111 and then transmitted through the metal thin-film filter 112, and outputs a detection signal corresponding to the amount (intensity) of the incident light. The detection signal output from the solid-state imaging element 113 is processed by the DSP 114 and the imaging element controller 115 before being supplied through the bus 116 to the signal processor 117.

The signal processor 117 performs various signal processes described below, such as a process of detecting a change in signal intensity (FIG. 7 etc.), a process of mapping a captured image (FIG. 8A etc.), etc. on the detection signal from the solid-state imaging element 113. The signal processor 117 also accesses the storage 118 via the bus 116 to record various items of data etc. thereto when necessary.

The microprocessor 119 controls, via the bus 116, parts of the image capture device 100, such as the imaging element controller 115, the signal processor 117, the light source controller 120, the filter controller 121, etc.

The light source controller 120 controls the light source 111 under the control of the microprocessor 119. As a result, electromagnetic waves having a narrow band of wavelengths are selectively emitted from the light source 111, such as an LED light source etc.

The filter controller 121 controls the metal thin-film filter 112 under the control of the microprocessor 119. As a result, for example, characteristics of the metal thin-film filter 112-1 can be changed.

The user interface 122 receives the user's instruction. The microprocessor 119 controls an operation of each part of the image capture device 100 based on the instruction to the user interface 122.

The image capture device 100 has the above configuration.

<Measurement Method to which the Present Technology is Applied>

Figure 4:
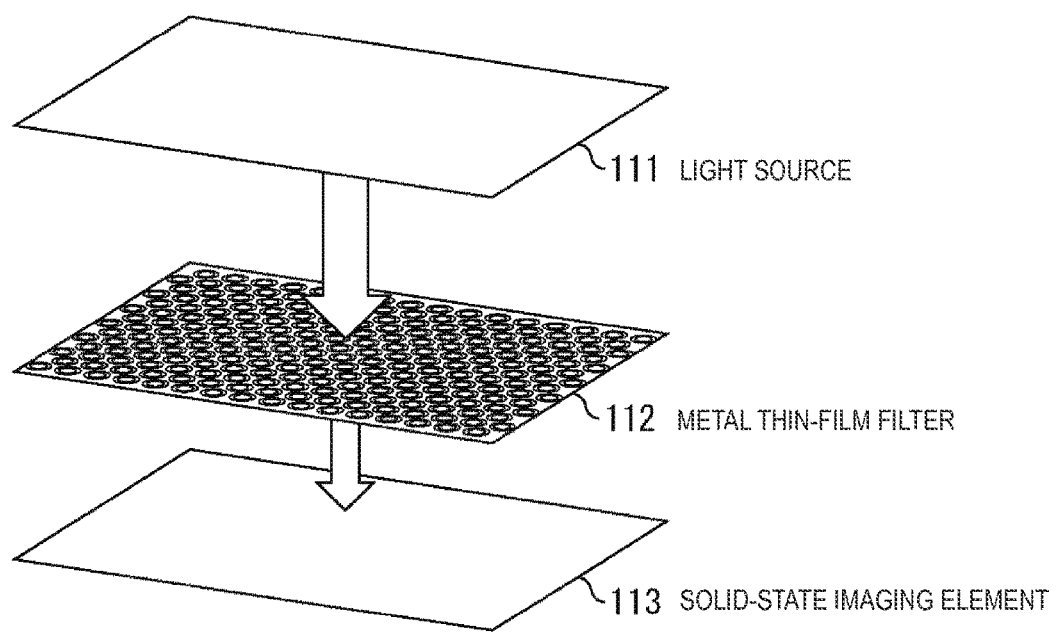
FIG. 4 is a diagram for describing the principle of measurement of a target object using the image capture device of FIG. 3.

FIG. 4 is a diagram for describing the principle of measurement of a target object by the image capture device 100 of FIG. 3.

As schematically shown in FIG. 4, the metal thin-film filter 112 is provided in the optical path between the light source 111 and the solid-state imaging element 113. As indicated by an arrow in FIG. 4, light emitted from the light source 111 is transmitted through the metal thin-film filter 112 and then received by the light receiving surface of the solid-state imaging element 113.

Figure 5:
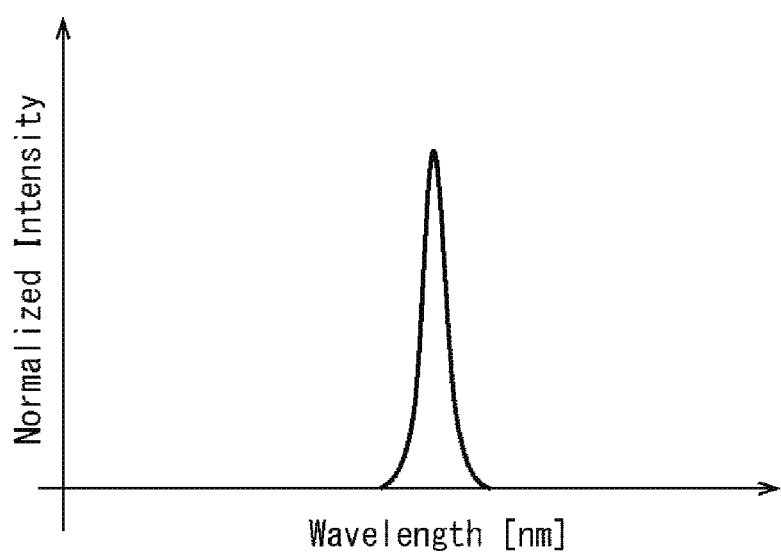
FIG. 5 is a diagram showing a spectrum of a narrow-band light source.

Here, as shown in FIG. 5, the light source 111 emits light having a particular narrow band of wavelengths within a wavelength band to which the solid-state imaging element 113 is sensitive. Note that the light having a particular narrow band of wavelengths has a half-width of not more than several tens of nanometers.

Figure 6:
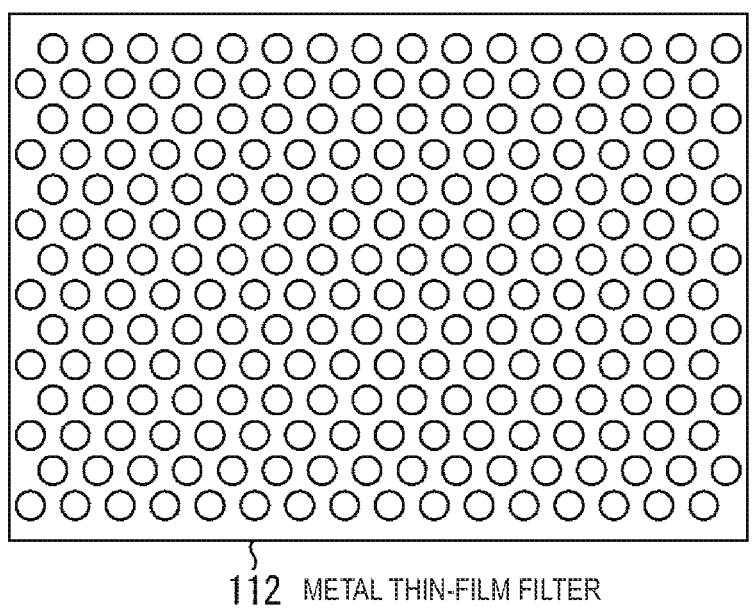
FIG. 6 is a diagram showing an example structure of a metal thin-film filter.

As shown in FIG. 6, the metal thin-film filter 112 has a periodic microstructural pattern on a sub-wavelength scale. In the example of FIG. 6, the metal thin-film filter 112 has a two-dimensional array of openings (holes) having a diameter smaller than a wavelength detected by the solid-state imaging element 113. The metal thin-film filter 112 has characteristic transmission properties attributed to the structure and metal thereof and the physical properties of a surrounding medium. Specifically, the metal thin-film filter 112 has a minute periodic structure in the metal surface thereof, and therefore, interference occurs due to surface plasmon polaritons generated at an interface between the metal thin-film surface and the surrounding medium, resulting in a transmission wavelength profile specific to the structure and the values of physical properties. The dispersion relation of surface plasmon polaritons depends on a complex refractive index between the metal and the medium which is present in the very vicinity of the metal surface (within the range of several hundreds of nanometers from the surface), and therefore, is highly sensitive to a change in the refractive index of the narrow region.

Because the metal thin-film filter 112 have such characteristics, if the refractive index of the surroundings in the very vicinity of the metal thin-film filter 112 changes, the spectral distribution of the transmitted light is shifted in the wavelength direction, so that the efficiency of transmission changes with respect to any particular wavelength of interest. If the intensity of light emitted from the light source 111 is the same, the intensity of a signal detected by the solid-state imaging element 113 is proportional to a change in the transmission efficiency. Therefore, by obtaining a change in the signal intensity, it can be determined whether or not viruses or bacteria are attached to antigens or antibodies immobilized on the surface of the metal thin-film filter 112.

Figure 7:
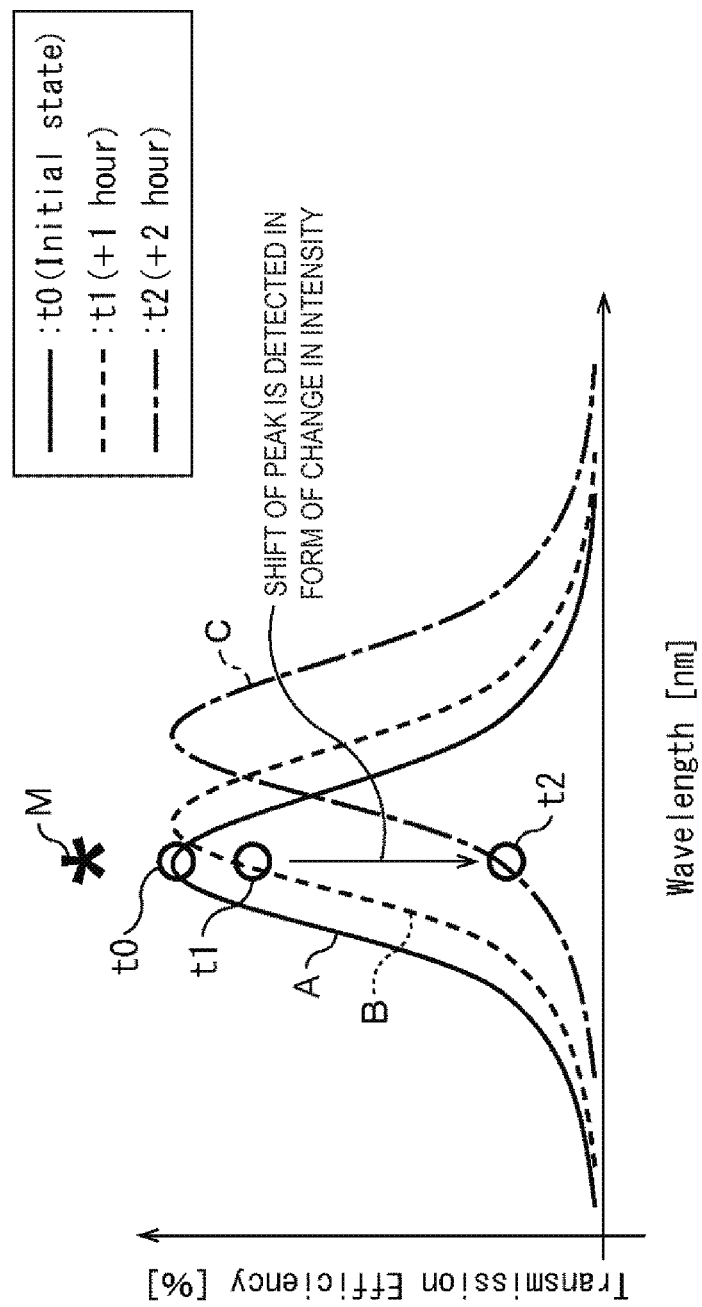
FIG. 7 is a diagram for describing the principle of detection of a change in signal intensity which corresponds to a change in transmission efficiency corresponding to a shift of a peak wavelength.

FIG. 7 shows an example transmission wavelength profile of the metal thin-film filter 112. As described above, the peak wavelength of the transmission spectrum is shifted to longer wavelengths as time passes. Here, it can be seen that, as the peak wavelength is shifted, the transmission efficiency changes with respect to a particular wavelength of interest at a position indicated by M in FIG. 7 as time passes, like transmission efficiencies at time t0 (initial state), time t1 (e.g., after one hour has passed), and time t2 (e.g., after two hours have passed).

In the solid-state imaging element 113, a change in the transmission efficiency is detected in the form of a change in the signal intensity. Specifically, the metal thin-film filter 112 has properties that the spectral distribution of the transmitted light is shifted in the wavelength direction due to a difference between the refractive index of a target object which is tightly attached or located close thereto and the refractive index of a medium with which a space therearound is filled. Therefore, the signal processor 117 detects a change in the signal intensity of the solid-state imaging element 113 as a change in the transmission efficiency which corresponds to the shift of the spectral distribution of the transmitted light in the wavelength direction.

Thus, in the image capture device 100, when a target object is measured, then if the surface light source 111 having a narrow band with a half-width of not more than several tens of nanometers is employed, a shift of the peak wavelength of the transmission spectrum, i.e., a change in the refractive index in the very vicinity of the metal surface of the metal thin-film filter 112, is detected in the form of a change in the signal intensity of the solid-state imaging element 113. Therefore, in the image capture device 100, even when a spectrometer is not provided, it can be determined whether or not viruses etc. are attached to antigens or antibodies immobilized on the surface of the metal thin-film filter 112. Therefore, compared to a device equipped with a spectrometer, a target object can be measured at low cost and with a simple configuration.

<Mapping of Captured Image>

Figure 8:
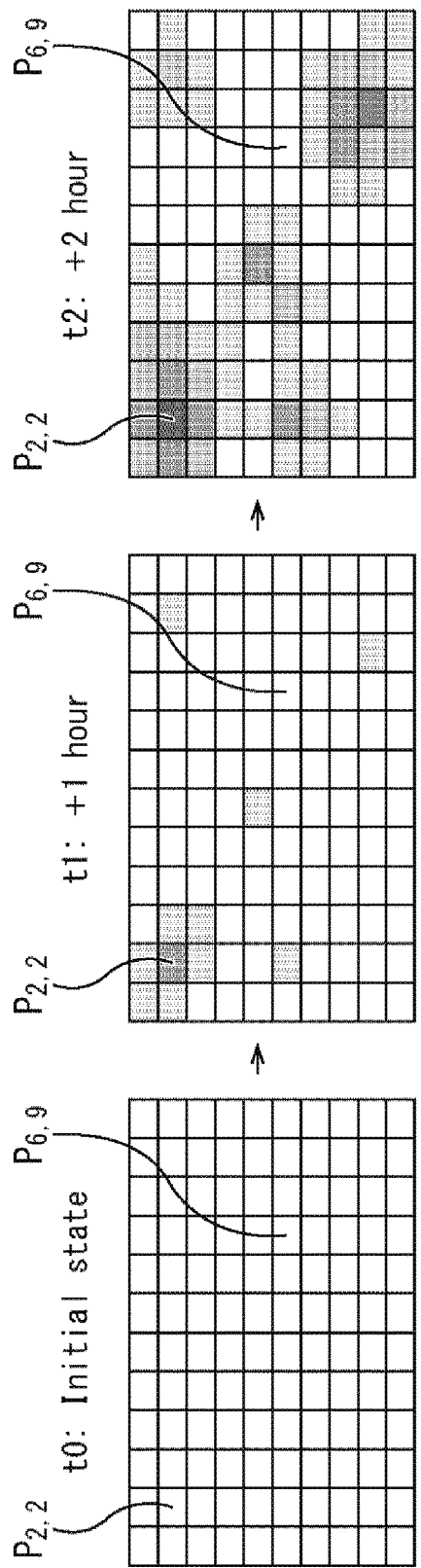
FIGS. 8A-C are diagrams for describing a change in signal intensity at a light receiving surface of a solid-state imaging element.

FIGS. 8A-8C are diagrams for describing changes in the signal intensity at the light receiving surface of the solid-state imaging element 113.

The solid-state imaging element 113 has an array of unit pixels including a photoelectric conversion element which generates an amount of electric charge corresponding to the amount of incident light. In FIGS. 8A-8C, for the sake of convenience, only a region of 10×12 pixels which is a portion of i×j pixels (where and j are an integer of one or more) in the array is shown. FIG. 8A shows a state of each pixel at time t0 (initial state). FIG. 8B shows a state of each pixel at time t1 (e.g., after one hour has passed). FIG. 8C shows a state of each pixel at time t2 (e.g., after two hours have passed).

In FIGS. 8A-8C, in each pixel, changes in the amount of incident light, i.e., changes in the signal intensity corresponding to changes in the refractive index (changes in the transmission efficiency) in the very vicinity of the metal surface of the metal thin-film filter 112, are represented by different shades. The shade increases with an increase in the change in the refractive index. In other words, FIGS. 8A to 8C show changes in the refractive index with time in a partial region of the metal thin-film filter 112 corresponding to the region of 10×12 pixels.

As shown in FIG. 8A, at time t0, viruses etc. are not attached to the metal thin-film filter 112, so that a change in the refractive index does not occur, and therefore, a change in the signal intensity does not occur. Thereafter, as shown in FIG. 8B, at time t1, a slight change in the refractive index occurs in a partial region, such as an upper left region etc., so that a corresponding change in the signal intensity is detected. Thereafter, as shown in FIG. 8C, at time t2, a change in the refractive index occurs in a large range, so that a corresponding change in the signal intensity is detected.

Figure 9:
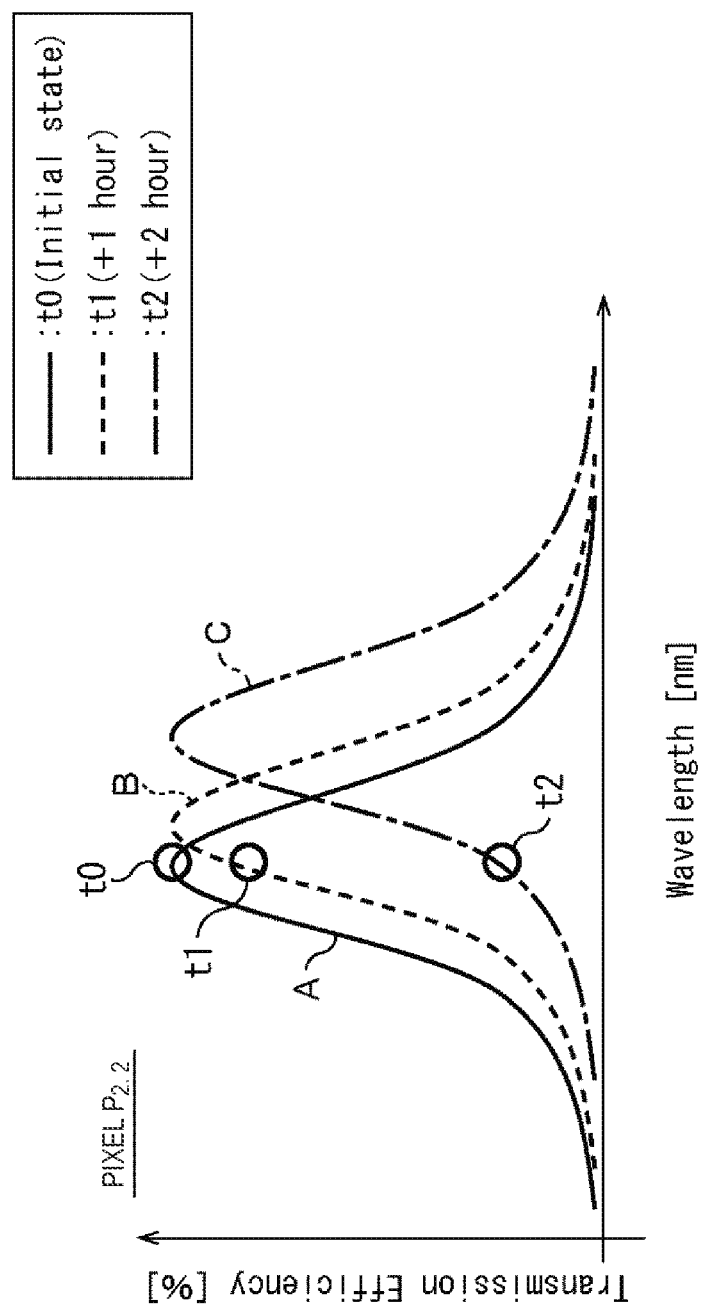
FIG. 9 is a diagram showing a transmission wavelength profile of a region corresponding to a pixel $P_{2,2}$ of interest.

Here, it can be seen that, for example, in a pixel $P_{2, 2}$ of interest in the region of 10×12 pixels shown in FIGS. 8A to 8C, the shade of the pixel increases with time, and therefore, a large change in the refractive index occurs. FIG. 9 shows a transmission wavelength profile of a region of the metal thin-film filter 112 corresponding to the pixel $P_{2, 2}$ of interest. As shown in FIG. 9, at time t0, a change in the refractive index does not occur, so that the transmission efficiency is high, and at time t1, a change in the refractive index occurs, so that the transmission efficiency slightly decreases. Thereafter, at time t3, a significant change in the refractive index occurs, so that the transmission efficiency significantly decreases.

Thus, in the pixel $P_{2, 2}$, the refractive index changes with time in a corresponding region of the metal thin-film filter 112. This change causes the peak wavelength of the transmission spectrum to be shifted, so that the transmission efficiency proportionately decreases. As a result, in the pixel $P_{2, 2}$, a detection signal is obtained which has a darker level than those of other pixels corresponding to regions in which a change in the refractive index does not occur.

Figure 10:
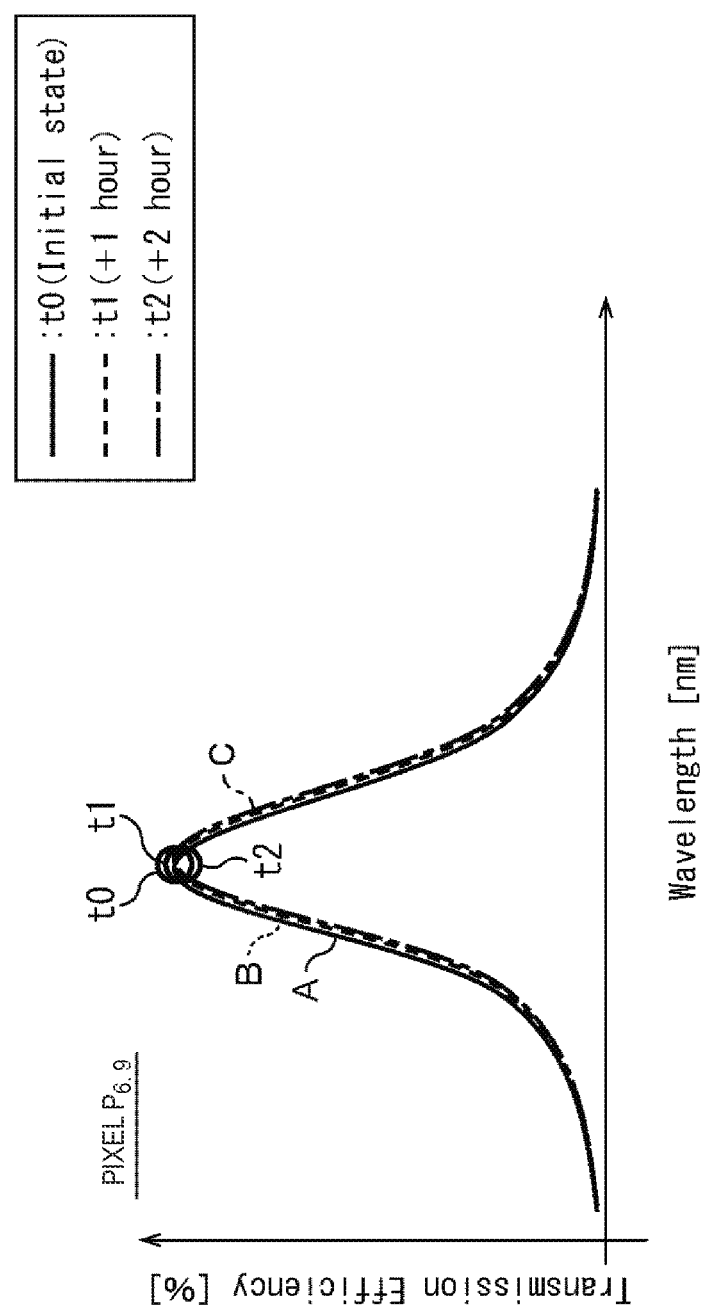
FIG. 10 is a diagram showing a transmission wavelength profile of a region corresponding to a pixel $P_{6,9}$ of interest.

Here, it can be seen that, for example, in a pixel $P_{6, 9}$ of interest in the region of 10×12 pixels shown in FIGS. 8A to 8C, the shade of the pixel does not change at all even after time has passed, and therefore, a change in the refractive index does not occur. FIG. 10 shows a transmission wavelength profile in a region of the metal thin-film filter 112 corresponding to the pixel $P_{6, 9}$ of interest. As shown in FIG. 10, at all times t0, t1, and t2, a change in the refractive index does not occur, so that the peak wavelength of the transmission spectrum is not shifted, and therefore, the transmission efficiency is substantially constant.

Thus, in the pixel $P_{6, 9}$, a change in the refractive index does not occur in a corresponding region of the metal thin-film filter 112 even after time has passed, and therefore, a corresponding shift in the peak wavelength of the transmission spectrum does not occur. As a result, the transmission efficiency does not substantially change, and in the pixel $P_{6, 9}$, a detection signal having a constant level is output.

The signal processor 117 obtains a captured image corresponding to such detection signals. Therefore, for example, if smoothing is performed using a plurality of captured images which are obtained at predetermined time intervals, or a difference between each of the captured images is calculated, a change in the signal intensity of a detection signal obtained from a pixel corresponding to a region where a change in the refractive index occurs, can be detected.

Although, in the example of FIGS. 8A-8C, only the region of 10×12 pixels is shown, a two-dimensional image can actually be obtained throughout the entire region of the metal thin-film filter 112 because a spatial resolution corresponding to the pixel side of the solid-state imaging element 113 is achieved. Also, because the solid-state imaging element 113 has an array of minute pixels having a pixel size of not greater than approximately several micrometers, changes in the refractive index in a region in the vicinity of the metal thin-film filter 112 can be two-dimensionally mapped at a high spatial resolution. As a result, the refractive index change can be detected at a high signal/noise (S/N) ratio.

<Simulation for Verifying Change in Transmission Efficiency>

Figure 11:
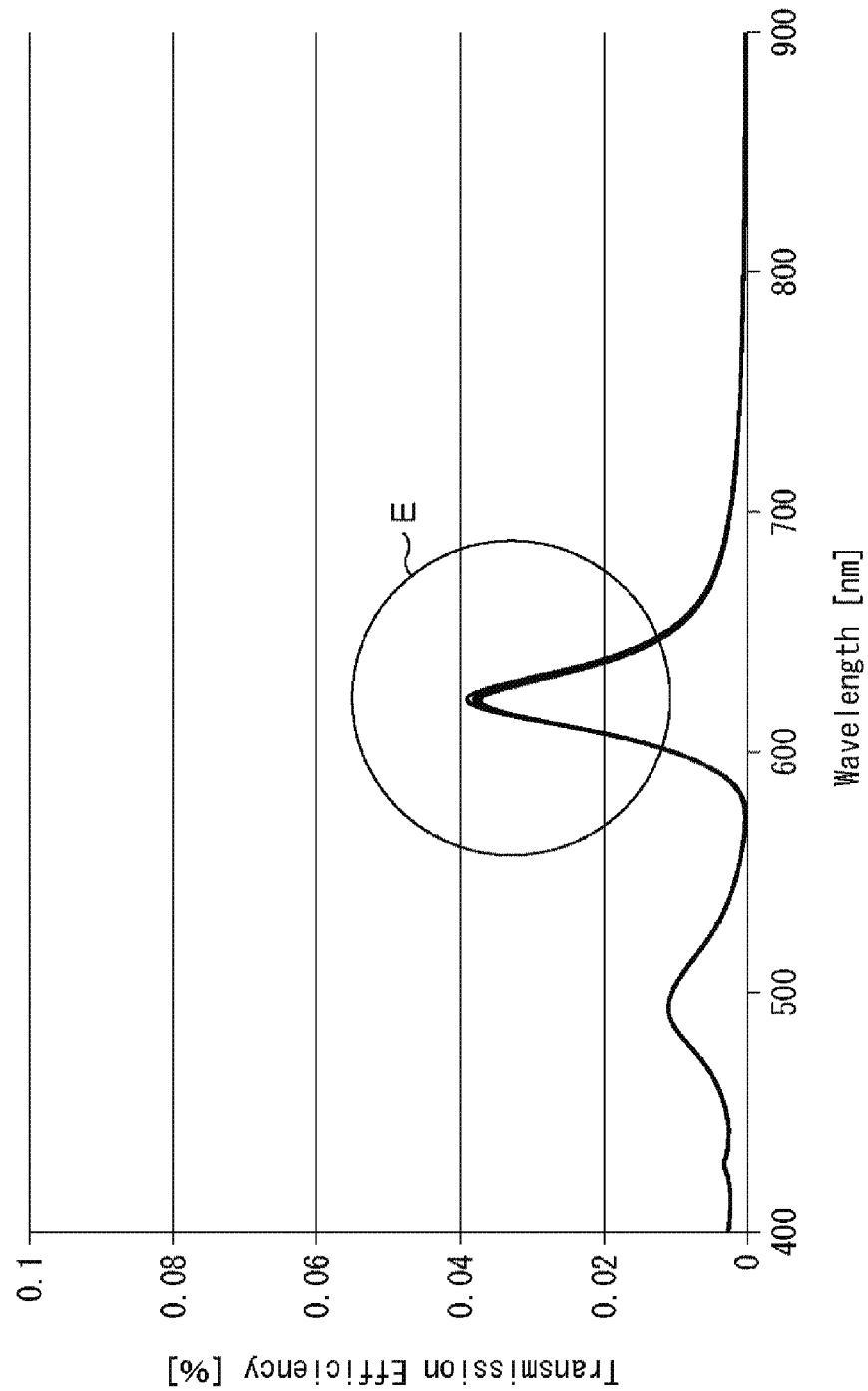
FIG. 11 is a diagram showing a transmission wavelength profile obtained as a result of a simulation.

FIG. 11 is a diagram showing a transmission wavelength profile of the metal thin-film filter 112 which is obtained as a result of a simulation conducted by the inventor of the present technology. In the simulation, the metal thin-film filter 112 is one which is a thin film of gold (Au) and has a two-dimensional array of openings (holes) as shown in FIG. 6 above.

Figure 12:
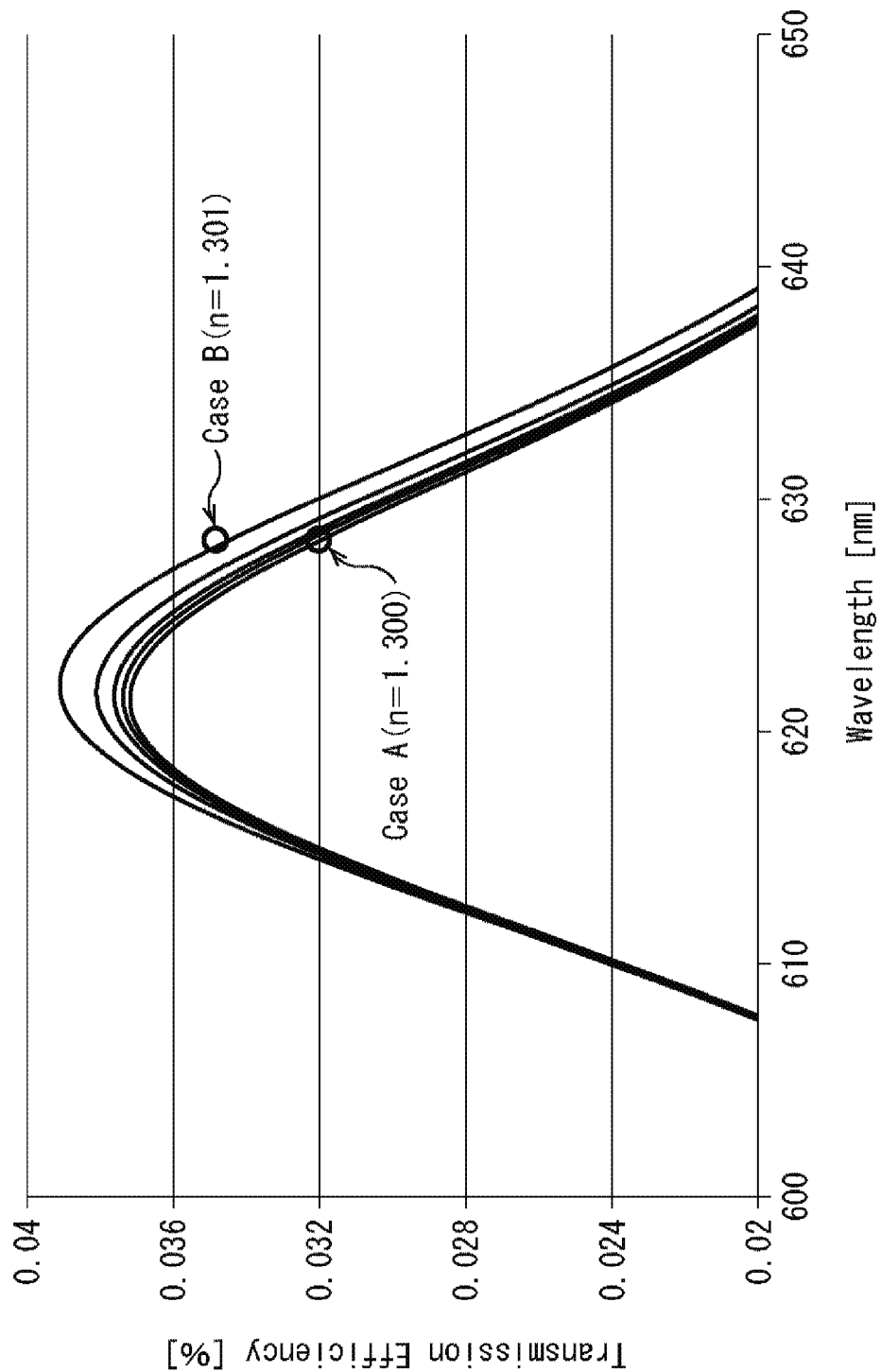
FIG. 12 is an enlarged view of a portion of the transmission wavelength profile of FIG. 11.

The transmission wavelength profile of FIG. 11 shows the result of the simulation indicating how the transmission efficiency and the peak wavelength shift of the metal thin-film filter 112 change when the refractive index n of a medium around the thin film in the thickness direction changes, for example, from 1.300 to 1.301. In this case, the amount of the peak wavelength shift is as small as about 1 nm. An enlarged view of a region E including a waveform around the peak wavelength is shown in FIG. 12. Specifically, as shown in the enlarged view of FIG. 12, it can be seen that, for example, at a particular wavelength of interest ($\lambda=628$ nm), when Case A (the refractive index n=1.300) is changed to Case B (the refractive index n=1.301), the amount of the peak wavelength shift is about 1 nm, but the transmission efficiency changes from 3.2% to 3.5%, i.e., by about 10%.

The change in the transmission efficiency is detected in the form of a change in the signal intensity of the solid-state imaging element 113. Therefore, for example, it can be determined whether or not viruses etc. are attached to antigen or antibodies immobilized on the surface of the metal thin-film filter 112.

<Division of Pixels into Blocks>

In the solid-state imaging element 113, the pixels arranged in the array may be divided into a plurality of blocks. In the metal thin-film filter 112, regions corresponding to adjacent blocks may be caused to have the same microstructural pattern. By calculating differences between signals detected by pixels in adjacent blocks, an offset between pixels may be corrected.

Figure 13:
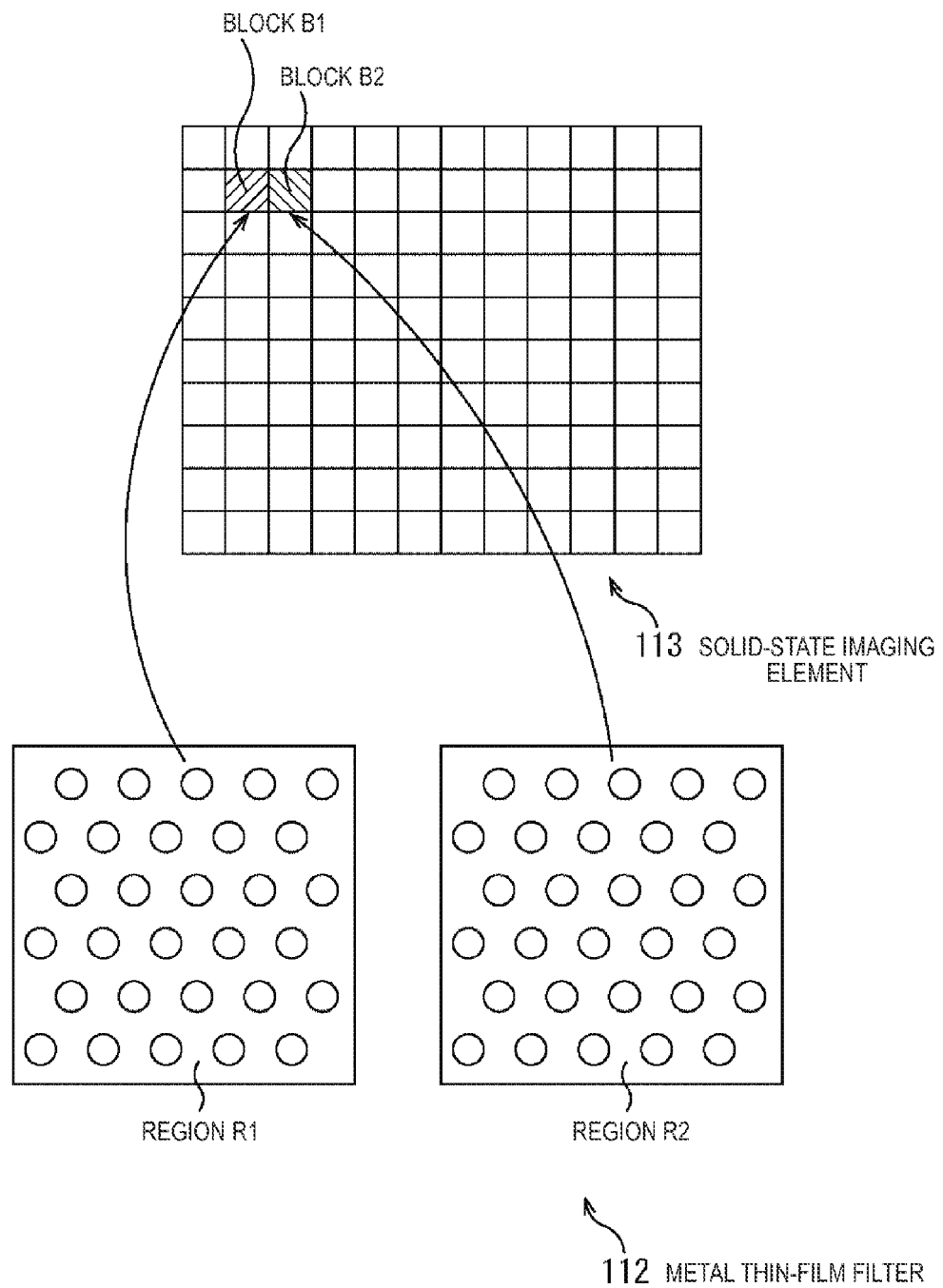
FIG. 13 is a diagram showing a relationship between a light receiving surface of a solid-state imaging element and regions corresponding to adjacent blocks.

Specifically, for example, as shown in FIG. 13, a region of 10×12 pixels which is a portion of i×j pixels provided in the pixel array unit, is assumed to be divided into a block B1 including a pixel $P_{2,2}$ and a block B2 including a pixel $P_{2,3}$. At this time, in the metal thin-film filter 112, a region R1 corresponding to the block B1 and a region R2 corresponding to the block B2 have the same microstructural pattern that has a two-dimensional array of openings (holes) as shown in FIG. 13.

Figure 14:
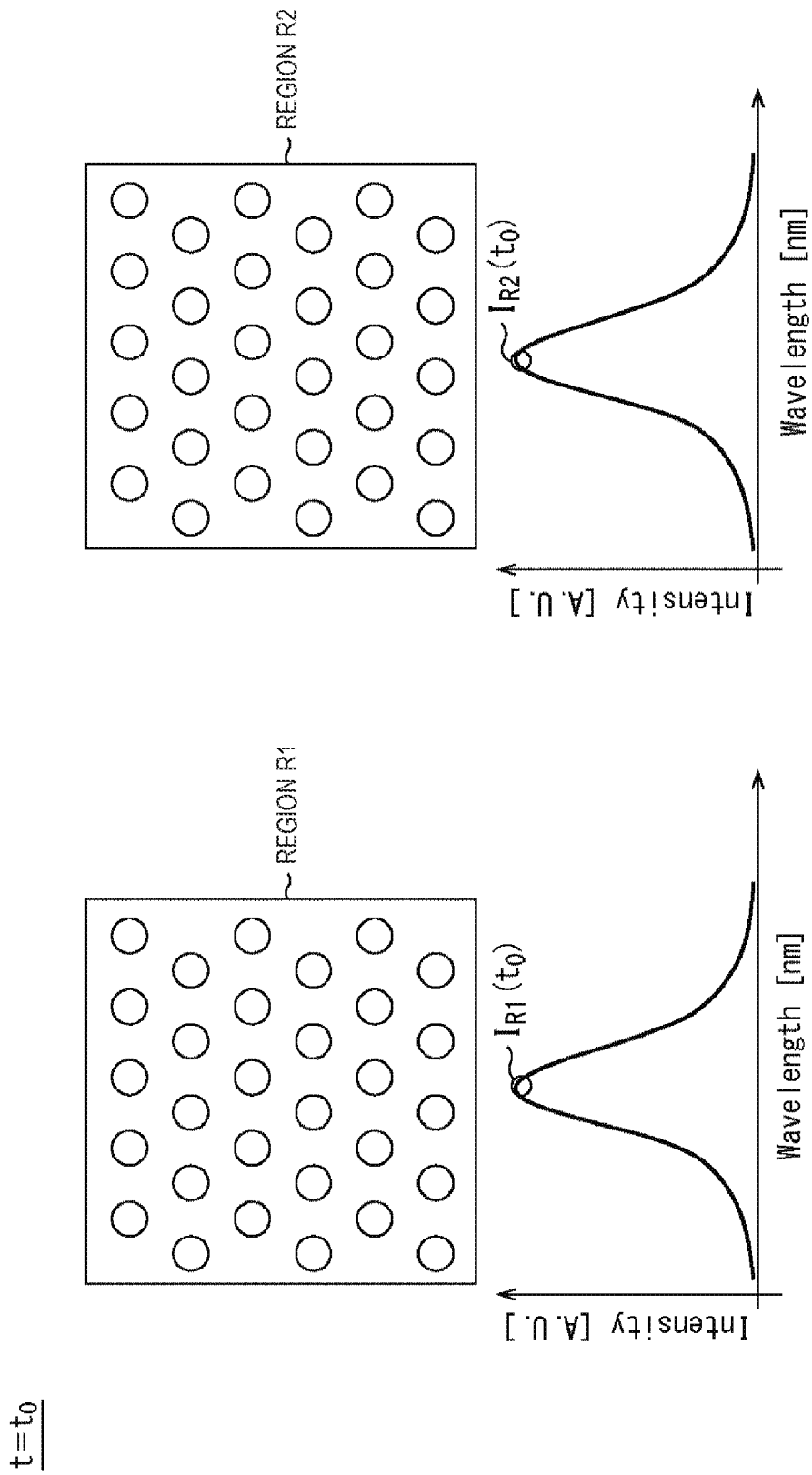
FIG. 14 is a diagram showing the intensity of light detected at pixels of each of adjacent blocks.

In this case, the amounts (intensities) of incident light to the blocks B1 and B2 of the solid-state imaging element 113 at time t0 (initial state) and time t1 (e.g., after one hour has passed, etc.) are shown in FIGS. 14 and 15.

At time t0, as shown in FIG. 14, viruses etc. are not attached to the region R1 or the region R2 of the metal thin-film filter 112, and therefore, the same light intensity is detected at the pixel $P_{2,2}$ included in the block B1 and the pixel $P_{2,3}$ included in the block B2. Therefore, detection signals obtained at the pixels $P_{2,2}$ and $P_{2,3}$ have the same level. Specifically, a difference between the level of the detection signal obtained in the block B1 corresponding to the region R1 and the level of the detection signal obtained in the block B2 corresponding to the region R2, at the time t0, may, for example, be calculated by:

$$\text{Signal Level}(t0)=IR1(t0)-IR2(t0) \quad (1)$$

Note that, in Expression (1), IR1(t0) and IR2(t0) have substantially the same value, and therefore, Signal Level(t0) is, for example, substantially zero.

Thereafter, at time t1, as shown in FIG. 15, viruses etc. ("TARGET OBJECT" in FIG. 15) are attached to the region R1 of the metal thin-film filter 112, so that a change in the refractive index in the very vicinity of the metal surface of the region R1 occurs. As a result, a change in the amount of incident light to the block B1 changes, so that a change occurs in the intensity of light detected by the pixel $P_{2,2}$. On the other hand, viruses etc. are not yet attached to the region R2 of the metal thin-film filter 112, so that a change in the amount of incident light to the block B2 corresponding to the region R2 does not occur between time t0 and time t1, and therefore, the same intensity of light is detected at the pixel $P_{2,3}$. Specifically, a difference between the level of the detection signal obtained in the block B1 corresponding to the region R1 and the level of the detection signal obtained in the block B2 corresponding to the region R2, at the time t1, may, for example, be calculated by:

$$\text{Signal Level}(t1)=IR1(t1)-IR2(t1) \quad (2)$$

Note that, in Expression (2), IR1(t1) and IR2(t1) have different levels of the detection signal detected in the block B1, and therefore, Signal Level(t1) has a value corresponding to a difference between the levels of the detection signal.

Thus, if, during a period of time from time t0 to time t1, for example, a change occurs in ambient temperature, the light intensity of the light source 111, or other conditions, a change occurs in the amount of incident light to the light receiving surface of the solid-state imaging element 113, so that a change occurs in the intensity of light detected at each pixel. Such a change in condition may add noise to a detection signal obtained at each pixel. However, if pixels are divided into blocks, regions corresponding to adjacent blocks are caused to have the same microstructural pattern, and differences between signals (signals corresponding to transmitted light components) detected at pixels in adjacent blocks are calculated, a direct current (DC) offset between pixels in both blocks can be corrected. As a result, a change in the signal intensity at a pixel having a change in the light intensity can be detected with high accuracy, and therefore, a change in the refractive index can be detected at a high S/N ratio, to obtain a captured image.

Although, in the foregoing, for the sake of convenience, it is assumed that each block includes a single pixel, each block may include one or more pixels.

<Specific Example Structure of Metal Thin-Film Filter>

The metal thin-film filter 112 uses the microstructural pattern to generate surface plasmon polaritons which are caused by coupling of free electrons with light at a particular electromagnetic wave wavelength. The metal thin-film filter 112 is a sub-wavelength structure which is obtained by microfabrication of a thin film of a conductive material having a plasma frequency in the wavelength band of ultraviolet light (specifically, preferably, gold (Au), silver (Ag), or aluminum (Al)). The metal thin-film filter 112 also has physical properties of a conductor, and a resonance wavelength which is determined by the period of the pattern, the diameter of the openings, the dot size, the film thickness, and the physical properties of a medium around the structure. Therefore, next, a specific example structure of the metal thin-film filter 112 will be described with reference to FIGS. 16 to 19.

(Hole Array Structure)

Figure 16:
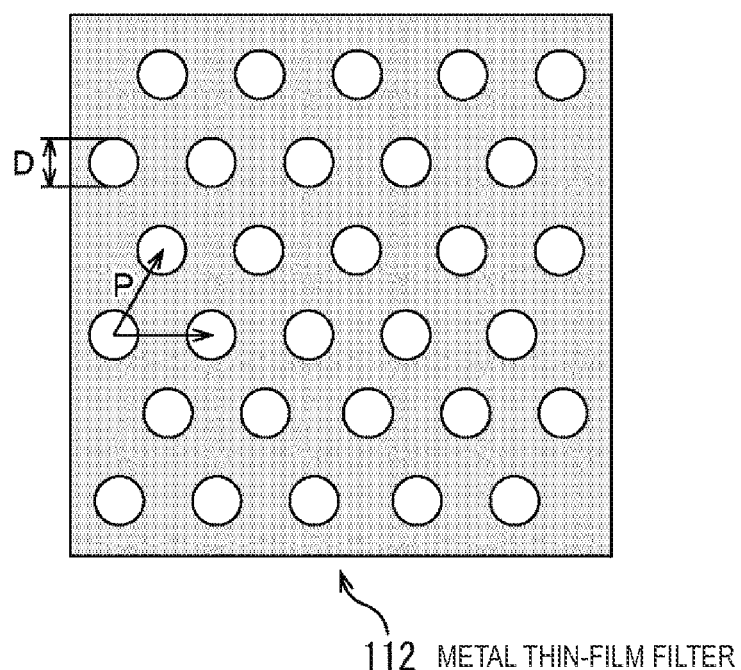
FIG. 16 is a diagram showing a metal thin-film filter having a hole array structure.

FIG. 16 is a diagram showing a case where a hole array structure is employed as the microstructural pattern of the metal thin-film filter 112.

As shown in FIG. 16, the hole array structure has a two-dimensional array of openings (holes) having a diameter smaller than a wavelength detected by the solid-state imaging element 113. The openings are preferably arranged in an array having a honeycomb structure (hereinafter referred to as a "honeycomb array") as shown in FIG. 16. The openings may be arranged in any other periodic array, such as an array having an orthogonal matrix (square matrix) structure (hereinafter referred to as an "orthogonal matrix array"). Note that the opening has a diameter D which is shorter than a wavelength of visible light, e.g., 500 nm or less. An interval between each opening, i.e., a fundamental period P of the periodic structure, is preferably, for example, about half the wavelength detected by the solid-state imaging element 113, specifically about 500 nm or less. The thin film has a thickness of, for example, about 500 nm or less.

(Dot Array Structure)

Figure 17:
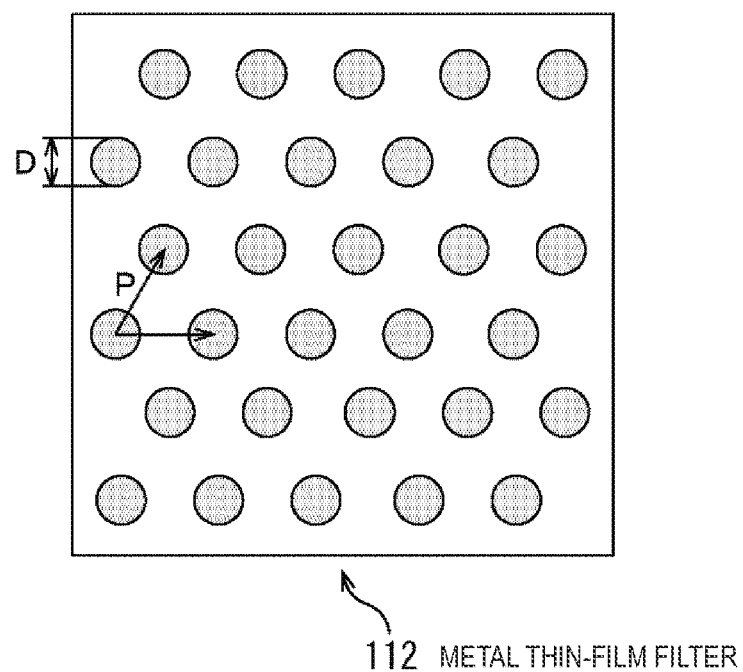
FIG. 17 is a diagram showing a metal thin-film filter having a dot array structure.

FIG. 17 is a diagram showing a case where a dot array structure is employed as the microstructural pattern of the metal thin-film filter 112.

As shown in FIG. 17, the dot array structure has a two-dimensional array of dots having a diameter smaller than a wavelength detected by the solid-state imaging element 113. The dots are preferably arranged in a honeycomb array as shown in FIG. 17. The dots may be arranged in any other periodic array, such as an orthogonal matrix array. Note that the dot has a diameter D which is shorter than a wavelength of visible light, e.g., 500 nm or less. An interval between each dot, i.e., a fundamental period P of the periodic structure, is preferably, for example, about 500 nm or less. The thin film has a thickness of, for example, about 500 nm or less.

(Coaxial Hole Array Structure)

Figure 18:
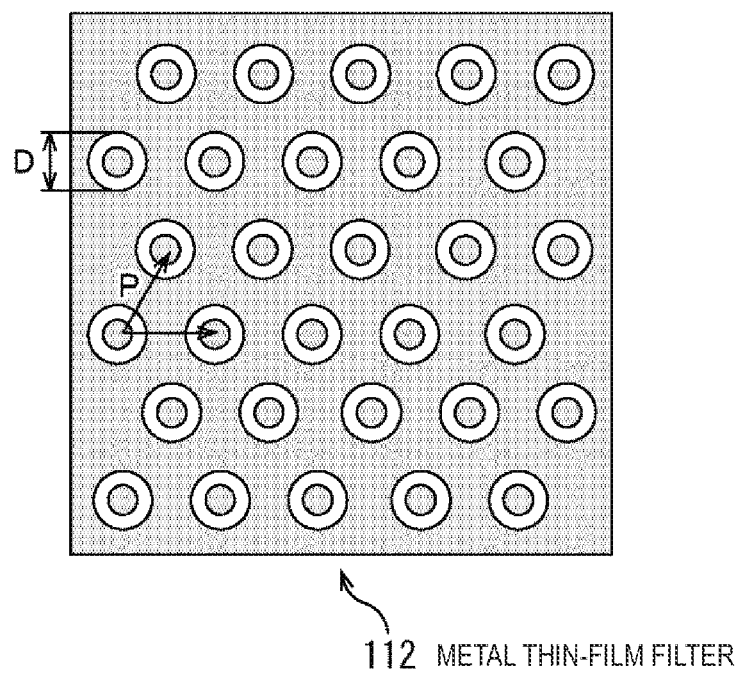
FIG. 18 is a diagram showing a metal thin-film filter having a coaxial hole array structure.

FIG. 18 is a diagram showing a case where a coaxial hole array structure is employed as the microstructural pattern of the metal thin-film filter 112.

As shown in FIG. 18, the coaxial hole array structure has a two-dimensional array of openings (holes) having a diameter smaller than a wavelength detected by the solid-state imaging element 113. The openings are preferably arranged in a honeycomb array as shown in FIG. 18. The openings may be arranged in any other periodic array, such as an orthogonal matrix array. A dot-like structure is provided at a center of each of the openings arranged in the two-dimensional array. Note that the opening has a diameter D which is shorter than a wavelength of visible light, e.g., 500 nm or less. An interval between each opening, i.e., a fundamental period P of the periodic structure, is preferably, for example, about 500 nm or less. The thin film has a thickness of, for example, about 500 nm or less.

(Ring Array Structure)

Figure 19:
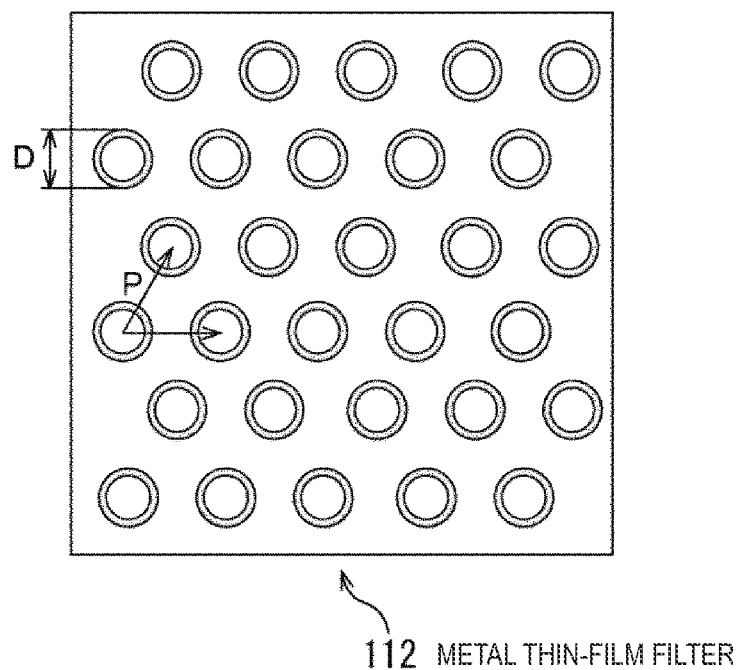
FIG. 19 is a diagram showing a metal thin-film filter having a ring array structure.

FIG. 19 is a diagram showing a case where a ring array structure is employed as the microstructural pattern of the metal thin-film filter 112.

As shown in FIG. 19, the ring array structure has a two-dimensional array of dots having a diameter smaller than a wavelength detected by the solid-state imaging element 113. The dots are preferably arranged in a honeycomb array as shown in FIG. 19. The dots may be arranged in any other periodic array, such as an orthogonal matrix array. Each of the dots arranged in the two-dimensional array has an opening having a diameter smaller than the diameter of the dot. Note that the dot has a diameter D which is shorter than a wavelength of visible light, e.g., 500 nm or less. An interval between each dot, i.e., a fundamental period P of the periodic structure, is preferably, for example, about 500 nm or less. The thin film has a thickness of, for example, about 500 nm or less.

Specific example structures of the metal thin-film filter 112 have been described above. Thus, the metal thin-film filter 112 has at least one periodic microstructural pattern in the surface thereof. The fundamental period of the microstructural pattern is not longer than approximately a wavelength of visible light. The metal thin-film filter 112 may have, as the microstructural pattern, only one of the above structures or a combination of two or more of the above structures.

<Method for Manufacturing Metal Thin-Film Filter>

A method for manufacturing the metal thin-film filter 112 of the image capture device 100 will now be briefly described. Note that the present technology is not limited to the manufacturing method below, and any method that can provide the structure of the metal thin-film filter 112 with high accuracy may be employed.

Initially, a flat and optically transparent substrate is prepared as a base on which the metal thin-film filter 112 is implemented. As a medium of a transparent insulating layer used in the wavelength band of visible light, silicon oxide ($SiO_2$) and a composite material including silicon oxide ($SiO_2$) as a main component are preferably used. In addition to this, magnesium fluoride ($MgF_2$) etc. may be used. Oxides and nitrides, such as silicon nitride ($Si_3N_4$), titanium oxide ($TiO_2$), tantalum oxide ($Ta_2O_5$), zirconium oxide ($ZrO_2$), niobium oxide ($Nb_2O_5$), hafnium oxide ($HfO_2$), etc., may be used although the refractive index increases.

A metal thin-film which is a base of the metal thin-film filter 112 is formed on the substrate by sputtering etc. A microstructure which imparts the filtering function to the metal thin-film is produced by a technique, such as electron beam lithography, EUV or UV lithography, interference exposure, etching, etc. Of the etching techniques, anisotropic dry etching is preferable. As a gas for etching, tetrafluoromethane ($CF_4$)-based etching gas is preferable. Sulfur hexafluoride ($SF_6$), trifluoromethane ($CHF_3$), xenon difluoride ($XeF_2$), etc. are also preferable. Note that a nano-stamper having a basic structure may be produced using electron beam lithography, and the structure may be transferred using a nano-printing technique.

<Configuration of Electronic Apparatus>

FIG. 20 is a diagram showing a configuration of an embodiment of an electronic apparatus to which the present technology is applied.

The electronic apparatus 300 is, for example, a mobile information apparatus or a mobile communication terminal, such as a mobile telephone, a smartphone, a tablet computer, etc. As shown in FIG. 20, the electronic apparatus 300 includes an image capture device 100, a controller 311, a memory unit 312, an operation unit 313, a display unit 314, a wireless communication unit 315, and an audio processor 316.

The controller 311 controls each part of the electronic apparatus 300. The memory unit 312 stores various items of data under the control of the controller 311.

The operation unit 313 supplies an operation signal corresponding to the user's operation to the controller 311. The controller 311 controls an operation of each part of the electronic apparatus 300 based on the operation signal from the operation unit 313. Note that the operation unit 313 may be a physical button, or alternatively, for example, a graphical user interface (GUI) image displayed on the screen of the display unit 314 having a touchscreen.

The display unit 314 includes a display device, such as a liquid crystal display (LCD) etc. The display unit 314 displays various items of information, such as a text, an image, etc., under the control of the controller 311.

The wireless communication unit 315 performs wireless communication with a predetermined server via a network, such as the Internet etc., under the control of the controller 311.

The audio processor 316 has devices for performing a conversation, such as a microphone, a loudspeaker, etc. The audio processor 316 performs an audio input process or an audio output process under the control of the controller 311.

The image capture device 100 has the configuration of FIG. 3. In the image capture device 100, a change in the refractive index in the very vicinity of the metal surface of the metal thin-film filter 112 is detected in the form of a change in the signal intensity of the solid-state imaging element 113, whereby a target object is measured. The result of the measurement of the target object is supplied to the controller 311. For example, the display unit 314 displays the result of the measurement of the target object under the control of the controller 311.

The electronic apparatus 300 has the above configuration.

As described above, according to the present technology, when a target object is measured, a shift of the peak wavelength of the transmission spectrum, i.e., a change in the refractive index in the very vicinity of the metal surface of the metal thin-film filter 112, is detected in the form of a change in the signal intensity of the solid-state imaging element 113. Therefore, a target object can be measured without providing a spectrometer.

Specifically, in measurement techniques in the related art, it is necessary to provide a spectrometer for detecting the amount of a shift of the peak wavelength of a transmission spectrum. In the measurement technique of the embodiment of the present technology, an LED light source etc. which emits light having a narrow band of wavelengths is employed as the light source 111, and the two-dimensional high-density solid-state imaging element 113 is provided immediately below the metal thin-film filter 112, whereby pixel information can be independently detected from each of pixels arranged in an array. Therefore, instead of the shift amount of the peak wavelength of a transmission spectrum, a change in state can be detected in the form of a change in signal intensity which corresponds to a change in transmission efficiency at a particular wavelength. Therefore, according to the measurement technique of the embodiment of the present technology, a target object can be measured at low cost and with a simple configuration, compared to measurement techniques in the related art, which use a spectrometer.

Although, in the foregoing, a filter using surface plasmon polaritons is referred to as a "metal thin-film filter," the filter may also be referred to as a "plasmonic filter."

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An image capture device including:
a narrow-band optical irradiation system including a light source;
a solid-state imaging element including an array of pixels and sensitive to a predetermined range of wavelengths; and
a metal thin-film filter provided in an optical path between the optical irradiation system and the solid-state imaging element, and having a periodic microstructural pattern having a period shorter than a wavelength detected by the solid-state imaging element.

(2) The image capture device according to (1), wherein the metal thin-film filter has a property that a spectral distribution of transmitted light is shifted in a wavelength direction due to a difference between the refractive index of a target object tightly attached or located close to the metal thin-film filter and a refractive index of a medium with which a space around the metal thin-film filter is filled, and the image capture device further includes a signal processor configured to detect a change in signal intensity of the solid-state imaging element, the change in signal intensity corresponding to a change in transmission efficiency corresponding to the shift of the spectral distribution of transmitted light in the wavelength direction.

(3) The image capture device according to (1) or (2), wherein
the metal thin-film filter is a thin film of an elemental metal or an alloy and having a thickness of 500 nm or less.
(4) The image capture device according to any one of (1) to (3), wherein
the metal thin-film filter has at least one periodic microstructural pattern in a surface of the metal thin-film filter, and a fundamental period of the microstructural pattern is not longer than approximately a wavelength of visible light.
(5) The image capture device according to (4), wherein
the metal thin-film filter has, as the microstructural pattern, a hole array structure including openings having a diameter of 500 nm or less arranged in a honeycomb array or an orthogonal matrix array.
(6) The image capture device according to (4), wherein
the metal thin-film filter has, as the microstructural pattern, a dot array structure including dot-like structures having a diameter of 500 nm or less arranged in a honeycomb array or an orthogonal matrix array.
(7) The image capture device according to (4), wherein
the metal thin-film filter has, as the microstructural pattern, a coaxial hole array structure including openings having a diameter of 500 nm or less arranged in a honeycomb array or an orthogonal matrix array, each opening having a coaxial structure in which a dot-like structure is provided at a center of the opening.
(8) The image capture device according to (4), wherein
the metal thin-film filter has, as the microstructural pattern, a ring array structure including dot-like structures having a diameter of 500 nm or less arranged in a honeycomb array or an orthogonal matrix array, each dot-like structure having a ring-like structure in which an opening having a diameter smaller than a diameter of the dot-like structure is provided at a center of the dot-like structure.
(9) The image capture device according to any one of (4) to (8), wherein
in the solid-state imaging element, the array of pixels is divided into a plurality of blocks,
in the metal thin-film filter, regions corresponding to adjacent blocks have the same microstructural pattern, and
the signal processor obtains a difference between signals detected by pixels in adjacent blocks to correct an offset between the pixels in the adjacent blocks.
(10) The image capture device according to any one of (1) to (9), wherein
the light source emits light having a narrow band of wavelengths.
(11) The image capture device according to (10), wherein
the light source is a light emitting diode (LED) light source or a laser light source configured to selectively emit electromagnetic waves having a narrow band of wavelengths of a wavelength band to which the solid-state imaging element is sensitive.
(12) The image capture device according to any one of (1) to (11), wherein
the solid-state imaging element is sensitive to a wavelength range of visible light or near-infrared light.
(13) The image capture device according to any one of (1) to (12), wherein
the metal thin-film filter is removably attached in the optical path.
(14) An electronic apparatus including:
an image capture device including
a narrow-band optical irradiation system including a light source,
a solid-state imaging element including an array of pixels and sensitive to a predetermined range of wavelengths, and
a metal thin-film filter provided in an optical path between the optical irradiation system and the solid-state imaging element, and having a periodic microstructural pattern having a period shorter than a wavelength detected by the solid-state imaging element.

What is claimed is:
1. An image capture device comprising:
a narrow-band optical irradiation system including a light source configured to emit light having a peak wavelength of a transmission spectrum;
an imaging element including an array of pixels divided into a plurality of blocks including at least a first block adjacent to a second block, wherein the imaging element is sensitive to light of a predetermined range of wavelengths, and wherein an edge of the first block borders an edge of the second block;

a metal thin-film filter provided in an optical path between the narrow-band optical irradiation system and the imaging element, wherein the metal thin-film filter includes a periodic microstructural pattern of an array of openings having a period shorter than a wavelength of light detected by the imaging element, wherein the metal thin-film filter includes a first region in the array of openings corresponding to the first block and a second adjacent region in the array of openings corresponding to the adjacent second block, the first region and the second adjacent region having the same microstructural pattern, and wherein a surface of the metal thin-film filter in each of the first region and the adjacent second region includes immobilized antigens or antibodies; and a signal processor configured to generate a signal based on a difference between an intensity of incident light at one or more pixels of the first block and an intensity of incident light at one or more pixels of the adjacent second block when a peak wavelength of a transmission spectrum of the incident light at the one or more pixels of the first block is different from the peak wavelength of the transmission spectrum of the light emitted from the light source and a peak wavelength of a transmission spectrum of incident light at the one or more pixels of the adjacent second block is the same as the peak wavelength of the transmission spectrum of the light emitted from the light source.

2. The image capture device according to claim 1, wherein the metal thin-film filter has a property that a spectral distribution of transmitted light is shifted in a wavelength direction due to a difference between a refractive index of a target object tightly attached or located close to the metal thin-film filter and a refractive index of a medium with which a space around the metal thin-film filter is filled, and the signal processor is configured to detect a change in signal intensity of the imaging element, the change in signal intensity corresponding to a change in transmission efficiency corresponding to the shift of the spectral distribution of transmitted light in the wavelength direction.

3. The image capture device according to claim 2, wherein the metal thin-film filter is a thin film of an elemental metal or an alloy and having a thickness of 500 nm or less.

4. The image capture device according to claim 3, wherein the metal thin-film filter has at least one periodic microstructural pattern in a surface of the metal thin-film filter, and a fundamental period of the microstructural pattern is not longer than approximately a wavelength of visible light.

5. The image capture device according to claim 4, wherein the metal thin-film filter has, as the microstructural pattern, a hole array structure including openings having a diameter of 500 nm or less arranged in a honeycomb array or an orthogonal matrix array.

6. The image capture device according to claim 4, wherein the metal thin-film filter has, as the microstructural pattern, a dot array structure including dot-like structures having a diameter of 500 nm or less arranged in a honeycomb array or an orthogonal matrix array.

7. The image capture device according to claim 4, wherein the metal thin-film filter has, as the microstructural pattern, a coaxial hole array structure including openings having a diameter of 500 nm or less arranged in a honeycomb array or an orthogonal matrix array, each opening having a coaxial structure in which a dot-like structure is provided at a center of the opening.

8. The image capture device according to claim 4, wherein the metal thin-film filter has, as the microstructural pattern, a ring array structure including dot-like structures having a diameter of 500 nm or less arranged in a honeycomb array or an orthogonal matrix array, each dot-like structure having a ring-like structure in which an opening having a diameter smaller than a diameter of the dot-like structure is provided at a center of the dot-like structure.

9. The image capture device according to claim 4, wherein the signal processor obtains a difference between a signal corresponding to the intensity of incident light at the one or more pixels of the first block and a signal corresponding to the intensity of incident light at the one or more pixels of the second block to correct an offset between pixels in the adjacent blocks.

10. The image capture device according to claim 1, wherein the light source emits light having a narrow band of wavelengths.

11. The image capture device according to claim 10, wherein the light source is a light emitting diode (LED) light source or a laser light source configured to selectively emit electromagnetic waves having a narrow band of wavelengths of a wavelength band to which the imaging element is sensitive.

12. The image capture device according to claim 1, wherein the imaging element is sensitive to a wavelength range of visible light or near-infrared light.

13. The image capture device according to claim 1, wherein the metal thin-film filter is removably attached in the optical path.

14. The image capture device according to claim 1, wherein at a second time subsequent to the generation of the signal, the signal processor is configured to generate a second signal based on a difference between the intensity of incident light at the one or more pixels of the first block due to viruses or bacteria attached to the antigens or antibodies immobilized on the surface of the metal thin-film filter in the first region and the intensity of incident light at the one or more pixels of the adjacent second block due to viruses or bacteria attached to the antigens or antibodies immobilized on the surface of the metal thin-film filter in the second region, wherein at the second time, the peak wavelength of the transmission spectrum of the incident light at the one or more pixels of the first block is different from the peak wavelength of the transmission spectrum of the light emitted from the light source, and the peak wavelength of the transmission spectrum of the incident light at the one or more pixels of the second adjacent block is different from the peak wavelength of the transmission spectrum of the light emitted from the light source.

15. The image capture device according to claim 10, wherein the narrow band of wavelengths has a half-width that is less than several tens of nanometers.

16. An electronic apparatus comprising:
an image capture device including:
a narrow-band optical irradiation system including a light source configured to emit light having a peak wavelength of a transmission spectrum,
an imaging element including an array of pixels divided into a plurality of blocks including at least a first block adjacent to a second block, wherein the imaging element is sensitive to light of a predetermined range of wavelengths, and wherein an edge of the first block borders an edge of the second block,
a metal thin-film filter provided in an optical path between the narrow-band optical irradiation system and the imaging element, wherein the metal thin-film filter includes a periodic microstructural pattern of an array of openings having a period shorter than a wavelength of light detected by the imaging element, wherein the metal thin-film filter includes a first region in the array of openings corresponding to the first block and a second region in the array of openings corresponding to the adjacent second block, the first region and the second region having the same microstructural pattern, and wherein a surface of the metal thin-film filter in each of the first region and the second region includes immobilized antigens or antibodies, and a signal processor configured to generate a signal based on a difference between an intensity of incident light at one or more pixels of the first block and an intensity of incident light at one or more pixels of the adjacent second block when a peak wavelength of a transmission spectrum of the incident light at the one or more pixels of the first block is different from the peak wavelength of the transmission spectrum of the light emitted from the light source, and a peak wavelength of a transmission spectrum of incident light at the one or more pixels of the adjacent second block is the same as the peak wavelength of the transmission spectrum of the light emitted from the light source; and a controller configured to receive the signal and cause a measurement based on the signal to be displayed on a display unit.

* * * * *